United States Patent [19]

Revici

[11] Patent Number: 4,565,689

[45] Date of Patent: Jan. 21, 1986

[54] METHOD FOR TREATING THE EFFECTS OF ALCOHOL

[75] Inventor: Emanuel Revici, New York, N.Y.

[73] Assignee: Wirth Maschinen-und Bohrgerate-Fabrik GmbH, New York, N.Y.

[21] Appl. No.: 722,870

[22] Filed: Apr. 12, 1985

[51] Int. Cl.[4] .................. A61K 31/21; A61K 31/095; A61K 31/105; A61K 31/265; A61K 31/045; A61K 33/04

[52] U.S. Cl. ..................................... 424/10; 424/162; 514/512; 514/513; 514/706; 514/707; 514/724; 514/738; 514/811

[58] Field of Search .................. 424/10, 162; 514/512, 514/513, 706, 707, 724, 738, 810, 812, 813

[56] References Cited

U.S. PATENT DOCUMENTS 4,346,082 8/1982 Revici ................................ 424/162

*Primary Examiner*—Stanley J. Friedman
*Attorney, Agent, or Firm*—Pennie & Edmonds

[57] ABSTRACT

A method for treating or aiding in the treatment of the manifestations of alcoholism or alcohol intoxication by aiding in the control of the craving for alcohol or by aiding in the control of alcohol withdrawal symptoms, or by aiding in the control of alcohol intoxication in a human which comprises internally administering to said human an effective amount of a compound having an active ingredient containing at least one bivalent negative sulfur to control said craving, symptoms, or intoxication so as to counteract the effects of alcohol.

13 Claims, No Drawings

METHOD FOR TREATING THE EFFECTS OF ALCOHOL

TECHNICAL FIELD

The invention relates to a method for eliminating or reducing the noxious effects of alcohol through the administration of catabolic sulfur-containing compounds.

DESCRIPTION OF THE PRIOR ART

There has been much recent interest in the study of alcoholism involving biological, psychological, and sociological investigations. Publications such as the various "Proceedings of the . . . Annual Alcoholism Conference" and "Recent advances in Studies of Alcoholism", obtainable from the Superintendent of Documents, U.S. Government Printing Office, Washington, D.C. 20402, indicate the rather intensive scientific investigations in this area.

An article by E. B. Truitt and M. J. Walsh appearing at p. 100 et sequa of "Proceedings of the First Annual Alcoholism Conference of the National Institute on Alcohol Abuse and Alcoholism", DHEW Publication No. (NIH) 74–675 (1973) discloses a number of chemicals and drugs which have been reported to have anti-alcohol effects. Included in this list are disulfuram (tetraethylthiuram disulfide—see also U.S. Pat. No. 2,567,814 Jacobsen et al), calcium carbimide (see also U.S. Pat. No. 2,998,350 de Grunigen et al), and thiocyanates which are used specifically for their anti-alcohol properties.

U.S. Pat. No. 3,860,719 to Marshall discloses the use of 2-[3,4-dichlorophenoxy)methyl]-2-imidazoline hydrochlorine (fenmetozole HCl) for combatting ethanol intoxication in mammals.

However, an article by H. B. McNamee et al "Fenmetozole in Acute Alcohol Intoxication in Man", *Clinical Pharmacology and Therapeutics* Vol. 17, Number 6, pp. 735–737 concludes that, within the scope of the subject study, fenmetozole does not antagonize or significantly modify acute effects of alcohol intoxification in humans.

Another publication entitled "Testing For a 'Sobering Pill'" DOT HS-801 288 (1974) available from National Technical Information Service, Springfield, Va. 22151 discloses that nikethamide, propranolol, L-dopa, pipradrol, aminophylline, ephedrine, sted-eze, and ammonium chloride were investigated to determine their potential for blocking or neutralizing the effect of alcohol on a human brain; the most effective amethystic agent found was L-dopa.

J. L. Mottin, in an article entitled "Drug-Induced Attenuation of Alcohol Consumption" *Quart J. Stud. Alc.* 34: 444–472 (1973) discussed, inter alia, the use of the following compounds re the subject title: disulfuram, citrated calcium cyanamide, and metronidazole.

Russian Inventor's Certificate 187250 discloses the use of the "thiolic" preparations—"unitol" and "dicaptol"—for use in treating alcoholism. The Merck Index (Eighth Edition) discloses that Dicaptol (BAL or British Anti-Lewisite) is 2,3-dimercaptopropanol and is marketed as a 10% solution in peanut oil with 20% benzyl benzoate. It is further asserted that in the U.S.S.R. a water soluble form is available under the name Unithiol and is 2,3-dimercapto-1-propanol sodium sulfonate.

U.S. Pat. No. 2,799,619 to Seifter et al. discloses compositions comprising certain phenothiazines as effective for treatment of alcoholics while British Pat. No. 1,399,992 (Revici) discloses that compositions comprising certain organic ethers are useful for the treatment of alcoholism.

U.S. Pat. No. 4,346,082, granted to the applicant on Aug. 24, 1982 discloses a method of treating alcoholism and for eliminating, reducing or preventing alcohol intoxication in humans by internally administering a therapeutic composition comprising an ammonium compound or compounds having a pH greater than 5.0 when placed in aqueous solution at a concentration of 5 grams per 100 grams of solution, and particularly, ammonium salt compounds comprising ammonium cations and sulfur anions.

Further U.S. Pat. No. 4,368,206, issued to applicant on Jan. 11, 1983 discloses an alternate method of treating alcoholism and for aiding in controlling alcohol intoxication in humans by the internal administration of a composition produced by heating certain allylically unsaturated compounds sufficient to substantially increase the peroxide titer. The incorporation of sulfur into these compositions during the heating process was found to be particularly advantageous.

Applicant has now discovered that a number of additional compounds are effective for treating the effects of alcohol.

SUMMARY OF THE INVENTION

The invention relates to a method for treating or aiding in the treatment of the manifestations of alcoholism or alcohol addiction by aiding in the control of the craving for alcohol or by aiding in the control of alcohol withdrawal symptoms or by aiding in the control of alcohol intoxification in a human by internally administering a compound with an active ingredient containing at least one bivalent negative sulfur in an amount sufficient to control the craving for alcohol or the symptoms caused by abstaining from it.

The most clinically effective compounds for this purpose are the hydropersulfides, alkyl sulfides, colloidal sulfur and organic thio compounds or their pharmaceutically acceptable salts. The most effective thio compounds to date are the thioglycerols and ethylenetrithio carbonate or their pharmaceutically acceptable salts.

These compounds are amenable to oral administration into the human body by mixing it with suitable binders or bulking materials, and placing an amount of the active material which is equal to a therapeutic dosage level into a pharmaceutical capsule.

The preferred therapeutic dosage level is about 100 milligrams of the active ingredient and the subject should be instructed to ingest a sufficient number of capsules to reduce or eliminate the desire to drink or to reduce or eliminate the affects of alcohol. The active ingredient may also be administered, however, by means of an injection, which allows the active ingredient to work more quickly, initially. The most clinically effective active ingredient is ethylene trithio carbonate and thioglycerols.

DETAIILED DESCRIPTION OF THE PREFERRED EMBODIMENTS

It is desirable to have a method for treating or aiding in the treatment of alcoholism in a human by controlling the craving for alcohol, by controlling withdrawal symptoms, or by aiding in the control of alcohol intoxication by humans. It is further desirable to have a method for aiding the control of alcohol intoxication of a non-alcoholic person by reducing or eliminating the effects alcohol intoxication upon him as well.

A series of tests run on alcoholic compounds by the applicant has shown them to possess a manifest anabolic action, due to the presence of a positively charged hydroxyl (OH) group. This anabolic action is also due to the solubility of the alcohols in lipids, which are fatty substances found in the human body. Due to the small number of carbon atoms which form the organic structure of ethyl alcohol ($CH_3CH_2OH$) and of other alcohols present in alcoholic beverages, the anabolic action referred to hereinabove is manifested at the higher levels of the body's hierarchic organization, i.e., mainly the organic and systemic levels.

Alcoholic compounds induce the typical anabolic manifestations, which include a preliminary excitation stage followed by a relaxant stage. The applicant has discovered that the adminstration of catabolic agent to a human subject, which is antigonistic to the anobolic effect of alcohol, is an extremely satisfactory technique for counteracting the subject's desire to drink. These agents therefore are indicated for the treatment of all of the manifestations following the intake of alcohol.

The applicant has discovered that certain catabolic agents, especially those active at higher levels of the body organization, are more specifically active than others against the physcological changes which occur in a human subject subsequent to the consumption of alcohol. The preferred catabolic agents for performing this function are bivalent negative sulfur compounds which clinical testing has shown to be the most efficacious agents.

The following specific compounds have been found to be particularly effective in clinical tests for eliminating or reducing the effects of alcohol consumption: hydropersulfides, alkyl sulfides, colloidal sulfur and organic thio products, mainly thioglycerols and ethylene trithio carbonate. The applicant's invention should not, however, be limited solely to the compounds listed above. The applicant has found that the most favorable results occur with the use of ethylene trithiocarbonate. The method for administration of these compounds may be through either the oral or parenteral route and it is important to note that the antianabolic action of these compounds is also manifested by an actual reduction in the amount of alcohol present in the blood of the subject. The dosage prescribed to a patient will, of course, vary depending upon the physical size and physiological characteristics of a particular patient and, since drinking patterns vary, the amount of alcohol consumed must also be taken into account in determining the correct dosage.

Generally speaking, however, for purposes of the preferred oral route of administration, the active material may be mixed with acceptable binders and bulking agents and therapeutic dosages of 100 milligrams, may then be placed in phamaceutical capsules for dispensing to a subject. For the average individual, a daily dosage of about 3-5 capsules containing 100 milligrams each of the active ingredient for the first 3 days after which the dosage level would be progressively lowered in accordance with the subject's reduced desire to drink. A heavy drinker may require as many as 8 capsules per day for the first 3-4 days, which could then be reduced to 3-4 capsules per day for the next four days. This should be a sufficient dosage to eliminate or reduce the subject's need for alcohol or to reduce or eliminate its effects after consumption.

As an alternate embodiment of the present invention, the compounds disclosed hrein may also be mixed with the compounds disclosed in U.S. Pat. No. 4,368,206. Therefore, the teachings of this patent are expressly incorporated herein.

While it is apparent that the invention herein disclosed is well calculated to fulfill the objects above stated, it will be appeciated that numerous modifications and embodiments may be devised by those skilled in the art, and it is intended that the appended claims cover all such modifications and embodiments as fall within the time spirit and scope of the present invention.

I claim:

1. A method for treating or aiding in the treating of the manifestations of alcoholism or alcohol intoxication by adding in the control of the craving for alcohol or by aiding in the control of alcohol withdrawal symptoms, or by aiding in the control of alcoholic intoxication in a human having said manifestations, craving, symptoms or intoxication which comprises internally administering to said human an effective amount of compound having an active ingredient of an organic compound containing at least one bivalent negative sulfur or its pharmaceutically acceptable salts to control said craving, symptoms, manifestations or intoxification so as to counteract the effects of alcohol.

2. The method of claim 1 wherein the active ingredient is a hydropersulfide, an alkyl sulfide, colloidal sulfur, an organic thio compound or one of their pharmaceutically acceptable salts.

3. The method of claim 2 wherein the organic thio compound is a thioglycerol, ethylene trithio carbonate, or one of their pharmaceutically acceptable salts.

4. The method of claim 1 wherein the active ingredient is administered orally.

5. The method of claim 1 wherein the active ingredient is administered by an injection.

6. The method of claim 1 wherein the active ingredient is mixed with suitable binder or bulking materials and an amount of the mixture equal to the therapeutic dosage level of the active ingredient is then enclosed within a pharmaceutical capsule.

7. The method of claim 6 wherein the therapeutic dosage level is about 100 milligrams of active ingredient per capsule.

8. The method of claim 7 wherein a sufficient number of pharmaceutical capsules are administered to a subject to reduce or eliminate the subject's desire to drink.

9. A method for treating or aiding in the treatment of the manifestations of alcoholism or alcohol intoxification by aiding in the control of the craving for alcohol or by aiding in the control of alcohol withdrawal symptoms, or by aiding in the control of alcohol intoxication in a human having said manifestations, craving, symptoms or intoxification which comprises internally administering to said human an effective amount of an organic thioglycerol, ethylene trithio carbonate, or colloidal sulfur or one of their pharmaceutically acceptable salts to control said craving, symptoms, manifestations or intoxication so as to counteract the effects of alcohol.

10. A method for treating or aiding in the treating of the manifestations of alcoholism or alcohol intoxication by aiding in the control of the craving for alcohol or by aiding in the control of alcohol withdrawal symptoms or by aiding in the control of alcohol intoxication in a human having said manifestations, craving, symptoms or intoxification which comprises orally administering to said human a sufficient number of pharmaceutical capsules daily, each capsule containing about 100 milligrams of an active ingredient which comprises a hydropersulfide, an alkyl sulfide, colloidal sulfur, an organic thio product or one of their pharmaceutically acceptable salts, to control said craving, symptoms, manifestations or intoxication so as to counteract the effects of alcohol.

11. A method for treating or aiding in the treating of the manifestation of alcoholism or alcohol intoxication by aiding in the control of the craving for alcohol or by aiding in the control of alcohol withdrawal symptoms or by aiding in the control of alcohol intoxication in a human having said manifestations, craving, symptoms, or intoxification which comprises orally administering to said human a sufficient number of pharmaceutical capsules daily, each capsule containing about 100 milligrams of ethylene trithio carbonate or its pharmaceutically acceptable salts to control said craving, symptoms, manifestations or intoxication so as to counteract the effects of alcohol.

12. The method of claim 10 wherein about 3-5 capsules are administered daily to said human.

13. The method of claim 11 wherein about 3-5 capsules are administered daily to said human.

* * * * *

UNITED STATES PATENT AND TRADEMARK OFFICE
CERTIFICATE OF CORRECTION

PATENT NO.   : 4,565,689
DATED        : January 21, 1986
INVENTOR(S)  : Emanuel Revici It is certified that error appears in the above-identified patent and that said Letters Patent is hereby corrected as shown below:

On the title page:
The Assignee of this patent is Elena Avram, New York, New York Signed and Sealed this Sixth Day of May 1986

[SEAL]

Attest:

DONALD J. QUIGG

Attesting Officer

Commissioner of Patents and Trademarks